United States Patent [19]

Schenk

[11] 4,439,522

[45] Mar. 27, 1984

[54] PROTEOLYTIC ENZYME COMPOSITION

[75] Inventor: Roy U. Schenk, Madison, Wis.

[73] Assignee: Bjorksten Research Laboratories, Inc., Madison, Wis.

[21] Appl. No.: 157,152

[22] Filed: Jun. 5, 1980

Related U.S. Application Data

[63] Continuation of Ser. No. 55,770, Jul. 9, 1979, abandoned, which is a continuation of Ser. No. 922,646, Jul. 7, 1978, abandoned, which is a continuation of Ser. No. 855,008, Nov. 25, 1977, abandoned, which is a continuation of Ser. No. 763,132, Jan. 27, 1977, abandoned, which is a continuation of Ser. No. 432,167, Jan. 10, 1974, abandoned.

[51] Int. Cl.³ .................. C12N 9/96; C12N 9/54; C07G 7/00; C12R 1/085
[52] U.S. Cl. ..................... 435/188; 435/221; 435/273; 435/834
[58] Field of Search ............. 435/188, 212, 221, 272, 435/273, 834

[56] References Cited

U.S. PATENT DOCUMENTS 3,775,254 11/1973 Buetow ........................ 435/221
3,860,485 1/1975 Schenk et al. ................ 435/221

OTHER PUBLICATIONS

Bjorksten, et al., Study of Low, Molecular Weight Proteolytic Enzymes, Finska Kemists, Medd. vol. 80, No. 4, 1971, pp. (70–87).
Schenk, et al., The Search for Microenzymes, Finska Kemists Medd., vol. 82, No. 2, 1973, pp. (26–46).
Kagan et al., Proteolysis of Elastin–Ligand Complexes, Biochemistry, vol. 11, No. 18, 1972, pp. (3412–3418).
Shapiro et al., Molecular Weight Estimation of Polypeptide Chains by Electrophoresis in SDS–Polyacrylamide Gels, Biochem. and Biophys. Res., Comm., vol. 28, No. 5, 1967, pp. (815–820).

Primary Examiner—David M. Nafe
Attorney, Agent, or Firm—Littlepage & Webner

[57] ABSTRACT

A proteolytic enzyme-containing composition is prepared having stabilized proteolytic enzyme activity and the ability to convert scleroproteins to water soluble products without racemization. The composition contains a proteolytic enzyme system from *Bacillus cereus* and an anionic detergent. The proteolytic enzyme system consists of a proteolytic enzyme oligomer that is retained by an ultrafilter membrane that retains molecules larger than 10,000 molecular weight and is reversibly interconvertible with a proteolytic active subcomponent that passes through the same membrane that retains the oligomer. The anionic detergent is preferably an alkyl sulfate or sulfonate or an alkyl-aryl sulfate or sulfonate.

1 Claim, No Drawings

PROTEOLYTIC ENZYME COMPOSITION

RELATED APPLICATIONS

This application is a continuation of Ser. No. 055,770, filed July 9, 1979, now abandoned; which is a continuation of Ser. No. 922,646, filed July 7, 1978, now abandoned; which is a continuation of Ser. No. 855,008, filed Nov. 25, 1977, now abandoned; which is a continuation of Ser. No. 763,132, filed Jan. 27, 1977, now abandoned; which is a continuation of Ser. No. 432,167, filed Jan. 10, 1974, now abandoned.

BACKGROUND AND PRIOR ART

It is well known that the detergent, sodium dodecyl sulfate (SDS) is a powerful denaturant of proteins. Recently it has been reported that this detergent accelerates the action of certain proteolytic enzymes for a short period of time, after which the enzyme, itself a protein, is destroyed by the detergent (H. M. Kagan et al., Biochemistry 11:3412. 1972).

OBJECTS OF THE INVENTION

An object of this invention is a novel, substantially stable, enzyme system capable of hydrolyzing hoofs, hair, feathers, gluten and the like proteins, without racemization of the resultant amino acids.

Another object is a substantially stable solution containing intimately intermixed an enzyme complex and an anionic detergent.

Further objects will become apparent as the following detailed description proceeds.

BRIEF STATEMENT OF THE INVENTION

I have discovered that several enzymes, characterized by interconvertibility with subcomponents having molecular weight ranges in the range 1,100–10,000 are resistant to denaturation by detergents which generally inactivate all other proteolytic enzymes, and furthermore, that such combinations between such detergents and enzyme systems, are much more effective in hydrolyzing hoofs, feathers, gluten, hair and and similar refractory proteinaceous material. than are any enzymes used alone for this purpose. Further, according to my invention, hydrolysis is effected without destroying 50% of the resultant amino acids by racemization, which occurs, for example, when strong acids are used as the hydrolyzing agents.

DETAILED DESCRIPTION

The present invention does not appear to require drawings for elucidation.

The following examples will illustrate specific embodiments of the invention, without intent to limit the same to these particular conditions.

It is well known that most anionic detergents are powerful denaturants for proteins. The most commonly used detergent for this purpose is sodium dodecyl sulfate, hereinafter referred to as "SDS" in keeping with the abbreviated terminology in common use.

I have now discovered that certain enzymes, characterized by at least partial reversible convertibility into monomers of molecular weights in the range of approximately 1,100–10,000 (Abstracts of the 166th meeting of the American Chemical Society, Microbiology Division, Paper No. 18, 1973.) (and Schenk & Bjorksten, Finska Kemists.Medd. Vol. 82, No. 2, 1973 (pp. 26–46) are remarkably stable to the denaturing effects of such detergents, and particularly to SDS; and that a combination of these particular enzymes with such anion active surface active agents, as typified by SDS, therefore can be practically used to rapidly and completely hydrolyze proteins which cannot otherwise be hydrolyzed economically without racemization of the component amino acids. Such racemization of the amino acids results in a value reduction of 50% because only one of the two active forms, usually the 1-form, is biologically active. The present invention has, therefore, a substantial economic value.

The application of the invention is illustrated by the following examples.

EXAMPLE 1

An enzyme, prepared from a strain of Bacillus cereus known as NRRL B-3869, deposited at the Northern Regional Research Laboratory of the U.S. Department of Agriculture, was prepared in accordance with the procedure described by R. Schenk and J. Bjorksten (ACS Abstracts, 166th Annual Meeting, Microbiology 18, 1973). It was subsequently passed through a column of DEAE Cellulose at pH 7.2. The resultant enzyme, having an apparent molecular weight of approximately 14,000 by the method of gel filtration (C. A. Williams and M. W. Chase, Methods in Immunology and Amino Chemistry 2, Chap. 9. Academic Press, New York. 1968) but of which at least 2% in moderate concentration or up to 10% in very dilute solution will pass through an Amicon Ultrafilter No. UM-10 due to equilibration with its low molecular weight subunits, was intermixed with 50 ml. of a 2% slurry of technical corn gluten. After the time intervals noted above, 5 ml. samples of the slurries were filtered, and 163 mg. of trichloroacetic acid was added to 3 ml. of filtrate to determine the amount of protein solubilized. The enzyme units shown in the tabulation below refer to Congocoll units by the method of W. L. Nelson et al. (Anal. Biochem. 2:39. 1961).

TABLE 1

Protein Solubilized from a 2% Slurry of Corn Gluten

Turbidity of Trichloroacetic Acid Treated Filtrates (495 nm):

| Treatment | Enzyme (60 units/ml.) | | No enzyme | |
|---|---|---|---|---|
| | Alone | Plus 0.1% SDS | Control | Plus 0.1% SDS |
| Hours | | | | |
| 0 | 0.031 | 0.030 | 0.021 | 0.044 |
| ½ | 0.055 | 0.003 | 0.027 | 0.053 |
| 1 | 0.092 | 0.003 | 0.015 | 0.090 |
| 2 | 0.120 | 0.172 | 0.013 | 0.080 |
| 4 | 0.215 | 1.36 | 0.017 | 0.070 |

It is thus seen that in 4 hours the above combination of the enzyme and SDS resulted in 530% greater solubilization of the protein than was obtained by the enzyme alone, the SDS alone being virtually inactive.

The test was continued, and after 22 hours tests showed that all of the protein present had been hydrolyzed by the enzyme-SDS combination of this invention, while the enzyme alone did not yet approach this result and the SDS alone had virtually no effect. After 5 hours in water solution with 0.1% SDS on the total weight, this enzyme still retained over 75% of its original activity.

EXAMPLE 2

A 2% gluten slurry, containing 75% protein by Kjeldahl assay, was treated with a mixture of 0.1% SDS and 120 units/ml. of proteolytic enzyme prepared from strain NRRL B-3869 of *B. cereus*. This combination was incubated at 34° C. and pH 8.3. The following values for soluble protein were obtained:

TABLE 2

| Hours | Soluble protein % |
|---|---|
| 0 | 15.2 |
| 3.5 | 52.6 |
| 5 | 74.6 |

The resultant polypeptides and amino acids were all in the active l-form. No racemization had taken place in the hydrolysis.

A control test made with the enzyme only, without SDS, showed 23% soluble protein after 5 hours, and SDS alone showed only a limited initial solubilization.

EXAMPLE 3

In order to compare the efficiency of the combination of the present invention with some of the best known and most used proteolytic enzymes, with and without SDS, I made the following experiments; using the same enzyme and conditions as described above in Example 2. Table 3 shows that papain and trypsin did not significantly increase the soluble protein after ½ hour whether alone or in the presence of SDS.

TABLE 3

Increase in Soluble Protein in Filtrates from a 2% Slurry of Corn Gluten
Turbidity at 495 nm following treatment with TCA

| Treatment | B. cereus NRRL-B3869 enzyme (60 units/ml.) | | Papain (0.4%) | | Trypsin (0.5%) | |
|---|---|---|---|---|---|---|
| | Alone | Plus 0.1% SDS | Alone | +0.1% SDS | Alone | +0.1% SDS |
| Hours (Reading at ½ hour used as blank) | | | | | | |
| 1 | 0.08 | 0.01 | 0.00 | −0.05 | −0.18 | 0.01 |
| 2 | 0.23 | 0.01 | 0.00 | −0.02 | −0.24 | 0.07 |
| 3 | 0.33 | 0.67 | 0.01 | −0.02 | −0.20 | −0.24 |
| 4 | 0.10 | 0.97 | 0.01 | — | — | −0.31 |

I next tested the solubilizing effects of high concentrations of a number of proteolytic enzymes on a 2% gluten suspension. The samples were run at pH 8.0 and 34° C. for 4 hours. The wet weights of the insolubles were determined (Table 4).

TABLE 4

Wet Weights of Insolubles from Gluten Treated with Several Proteolytic Enzymes

| Enzyme | Wet Weight of Insolubles |
|---|---|
| B. cereus enzyme, 58 units/ml. (0.02%) | 5.7 |
| As above, +0.1% SDS | 3.6 |
| As above, +0.02% Sodium laurate | 4.7 |
| Trypsin, 0.05%, 1 × crystallized | 7.8 |
| Chymotrypsin, 0.02%, crystalline | 7.8 |
| Bromelain, 0.1%, 2810 Rorer units/mg. | 6.8 |
| Pronase, 0.1%, 750 tyrosine units/mg. | 6.2 |

These results show that the novel *B. cereus* enzyme dissolved more protein than did the other enzymes; and that the SDS and the sodium laurate further enhanced the solubilization. Since I have obtained activities as high as 300 units/mg with the *B. cereus* enzyme, it was used at a level of less than 0.02%.

The stability of proteolytic activity of trypsin was then compared to that for a representative member of the new class of enzymes over a period of time. The results (Table 5) show that the activity of trypsin declined rapidly. In the presence of SDS the decline was precipitous. The presence of substrate retarded this decline only minimally. On the other hand, the oligomeric enzyme from strain NRRL B-3869 of *B. cereua* retained its activity over a prolonged period of time, even in the presence of SDS. Indeed, in the presence of substrate, the proteolytic activity was retained at a substantial level for 2 days (47 hours) even in the presence of SDS.

TABLE 5

Proteolytic Activity of Trypsin and of *B. cereus* Enzyme. In Aqueous Solutions with and without 0.04% SDS and 0.8% Substrate.

Percent of Original Activity (by Congocoll Assay)

| Hours | Alone | +SDS, Trypsin, 0.03% | +SDS & Substrate |
|---|---|---|---|
| 0 | 100 | 100 | 100 |
| 0.5 | 51 | 2 | 9 |
| 1.0 | 31 | 0 | 8 |
| | Representative of new class of enzymes 1,800 units/ml. | | |
| 0 | 100 | 100 | 100 |
| 1 | 79 | 40 | 94 |
| 2 | 48 | 29 | — |
| 5 | 43 | 5 | 94 |
| 23 | 2.4 | 0.2 | 44 |
| 47 | 0.7 | 0.1 | 22 |

EXAMPLE 4

In an effort to determine if the oligomeric low molecular weight proteases of this invention are effective on insoluble proteins in general, the activity of one of the enzymes, with and without SDS, was compared to trypsin in its ability to solubilize feathers. The results, shown in Table 6, demonstrated that the enzymes used in the present invention, in the presence of an anion active surfactant, are far more effective than a representative enzyme previously considered for this purpose.

It is thus seen that a representative enzyme used in prior art will not dissolve even approximately similar percentages of the protein as will the enzymes of the present invention. SDS was not added to this other enzyme because it is rapidly inactivated by it.

TABLE 6

Solubilization of a 1% Slurry of Feathers by Proteolytic Enzymes

| Enzyme | % of Feather Solubilized | |
|---|---|---|
| Trypsin 0.1% | 36 | Optical check revealed that no racemization had taken place. |
| Oligomeric low molecular weight enzyme from B. cereus 4,400 units/ml. +0.02% SDS | 60 66 | |
| No enzyme | 0 | |

Since both sodium dodecyl sulfate and sodium laurate were effective in enhancing the activity of the new class of enzymes, tests of other surfactants appeared to be desirable. I prepared samples of sodium salts of the 4 carbon through 10 carbon fatty acids, and of sodium alkyl aryl sulfonate (Sulframin AOS 90 of Witco Chemical Corp.) for comparison with the activity of SDS. These were added to 2% slurries of gluten containing 185 units of enzyme per ml. Solubilization was evaluated by measuring the increase in absorbance at 280 nm (protein absorption peak). Table 7 shows that the alkyl aryl sulfonate enhanced the solubilization of the protein as well as did the SDS. The fatty acid salts showed limited assistance to solubilization, but were not as effective as were the two sulfate containing detergents.

TABLE 7

Solubilization of 2% Gluten Slurry by Oligomeric, Low Molecular Weight Enzyme with Differing Surfactants.

| Surfactant Used | Increase in Absorbance at 280 nm | | |
|---|---|---|---|
| | 1 Hour | 2 Hours | 5.7 Hours |
| None | 0.5 | 3.5 | 6.5 |
| 0.2% Sodium butyrate | 1.0 | 4.0 | 7.5 |
| 0.2% Sodium caproate | 0.5 | 4.0 | 7.0 |
| 0.2% Sodium caprylate | 1.0 | 4.0 | 8.0 |
| 0.2% Sodium caprate | 0.5 | 3.5 | 7.0 |
| 0.2% Alkyl aryl sulfonate | 4.5 | 8.0 | 12.0 |
| 0.1% SDS | 4.5 | 9.0 | 11.0 |

While the examples have centered on a particular enzyme, the best studied of the group discussed, it has nonetheless been established that other enzymes characterized by reversible relationship between monomers and oligomers and low molecular weight, possess similar properties and respond synergistically to the compounding with surface active agents such as those mentioned above.

For example, enzymes have been prepared from other spore forming organisms, which apparently have a relationship to the sporulation, or to the germination of the spores. While I do not wish to be confined to any particular theory, it is my belief that the subject enzymes have evolved from the necessity of spore forming microorganisms to create enzymes which make possible the manipulation of the extremely dense spore shells, in which closely packed crosslinkages sterically hinder the action of any enzymes, except those which are able to dissociate into exceptionally low molecular weight subunits (Mol. wt. in the range 1,100 to 6,500 and even sometimes up to 10,000) as determined by a method modified from R. T. Swank & K. D. Munkres (Anal. Biochem. 39:462. 1971).

Such enzymes can be obtained from several bacteria, screened for this purpose as described by Bjorksten, Weyer and Ashman (Finska Kemists. Medd. 80: 70. 1971). Of such organisms several were found to be good producers of enzymes suitable for the present invention. While these have not yet been taxonomically identified, they are all spore-forming organisms, and the optimal phase for harvest in the production cycle is either shortly before, during, or shortly following incipient sporulation, confirming the view that these enzymes have a relation to spore formation and spore germination processes. These other organisms are all distinct from B. cereus, because their growth is inhibited by Polymixin sulfate, and because their microscopic appearance differs from B. cereus. They are available from the U.S. Dept. of Agriculture, Northern Marketing and Nutrition Research Division, 1815 University Street, Peoria, Ill. 61604, under designations NRRL-B-5468, NRRL-B-5470, NRRL-B-3867, NRRL-B-3868, NRRL-B-3870, respectively.

Any of these organisms, cultured under the conditions described by J. Bjorksten, E. R. Weyer and S. M. Ashman (Finska Kemists. Medd. 80: 75, 76. 1971.) will produce enzyme systems which are characterized by interconvertibility with subcomponents having molecular weights in the range 1,100–10,000 Mol. wt. (determined by the modified Swank & Munkres method mentioned above), by high activity about pH 7 and high stability in the presence of anionic detergents, and further by enhanced activity in proteolysis of scleroproteins in the presence of such detergents.

Among the various anionic detergents, the alkyl sulfates and sulfonates and the alkyl-aryl sulfates and sulfonates have been found particularly effective. Among the latter, "Sulframine AOS 90" made by Witco Chemical Corp. may be mentioned as a specific example, although a multitude of similar if not identical products are available from various sources.

These enzyme systems are also characterized by the fact that an increasing percentage of the enzyme will pass through a UM-10 membrane as the enzyme is diluted. As is well known to those skilled in the art, this is typical behavior, based on the law of mass action, for an equilibrium system in which a monomer small enough to pass through the membrane (i.e., less than mol. wt. 10,000) is in equilibrium with one or more oligomers that will not pass through the membrane (i.e., larger than mol. wt. 10,000).

They are all capable of hydrolyzing scleroproteins such as feathers, hoofs, hair, including also gluten and similar highly crosslinked proteinaceous aggregates without any racemization of the hydrolysis products, to water soluble products, when compounded with anionic surface active agents as above described. These water soluble products may be amino acids, peptides, or related hydrolysis products from scleroproteins. Some increase in rate of hydrolysis is apparent even on addition of as little as 0.05% of detergent on the weight of solid proteinaceous substrate present, the preferred range being 0.5–5%; larger percentages may be used, but are generally uneconomical.

Having thus disclosed by invention, I claim:

1. A proteolytic enzyme-containing composition having stabilized proteolytic enzyme activity and the ability to convert scleroproteins to water soluble products without racemization consisting essentially of an anionic detergent selected from the group consisting of alkyl sulfates, alkyl sulfonates, alkyl-aryl sulfates and alkyl-aryl sulfonates, and an enzyme system consisting of a proteolytic enzyme oligomer derived from Bacillus cereus that is retained by an ultrafilter membrane that retains molecules larger than 10,000 molecular weight and is reversibily interconvertible with a proteolytic active subcomponent that passes through the same membrane that retains the oligomer, said enzyme system retaining more than 75% of its proteolytic activity for at least 5 hours when said composition is mixed with a 2% corn gluten slurry and said enzyme system converts said corn gluten to water soluble products during said 5 hours.

* * * * *